United States Patent
Greenslet et al.

(10) Patent No.: US 9,999,500 B2
(45) Date of Patent: Jun. 19, 2018

(54) ANTI THROMBOGENIC HEART VALVE AND MEDICAL IMPLEMENTS

(75) Inventors: Hitomi Greenslet, Gainesville, FL (US); Faris M. Al-Mousily, Gainesville, FL (US); Abdullah A. Kendoush, Augusta, GA (US)

(73) Assignee: University of Florida Research Foundation, Inc., Gainsville, FL (US)

(*) Notice: Subject to any disclaimer, the term of this patent is extended or adjusted under 35 U.S.C. 154(b) by 5 days.

(21) Appl. No.: 14/004,213

(22) PCT Filed: Mar. 12, 2012

(86) PCT No.: PCT/US2012/028764
§ 371 (c)(1),
(2), (4) Date: Dec. 30, 2013

(87) PCT Pub. No.: WO2012/122567
PCT Pub. Date: Sep. 13, 2012

(65) Prior Publication Data
US 2014/0128960 A1 May 8, 2014

Related U.S. Application Data

(60) Provisional application No. 61/451,201, filed on Mar. 10, 2011, provisional application No. 61/538,874, filed on Sep. 25, 2011.

(51) Int. Cl.
*A61F 2/24* (2006.01)
*B29C 39/00* (2006.01)
(Continued)

(52) U.S. Cl.
CPC .......... *A61F 2/2412* (2013.01); *A61F 2/2415* (2013.01); *A61F 2/82* (2013.01);
(Continued)

(58) Field of Classification Search
CPC .......................... A61F 2/24; A61F 2250/0025
See application file for complete search history.

(56) References Cited

U.S. PATENT DOCUMENTS

| 3,886,947 A | 6/1975 | Sawyer |
| 4,339,831 A | 7/1982 | Johnson |

(Continued)

FOREIGN PATENT DOCUMENTS

| WO | 0021469 A1 | 4/2000 |
| WO | 0154625 A1 | 8/2001 |

OTHER PUBLICATIONS

Prasad B, Brook M, Smith T, Zhao S, Chen Y, Sheardown H, D'Souza R, Rochev Y; Mar. 19, 2010; Elsevier; Biointerfaces 78; pp. 237-242.*

(Continued)

*Primary Examiner* — Jacqueline Woznicki
(74) *Attorney, Agent, or Firm* — Timothy H. Van Dyke; Beusse, Wolter, Sanks & Maire PLLC

(57) ABSTRACT

Disclosed herein are heart valves made from a polymeric material, such as silicone. Specifically exemplified are heart valve embodiments made from a one or two-pieces of material, or which have low thrombogenic potential. Also disclosed are methods of fabricating such valves. Furthermore, also disclosed are systems for testing performance of heart valves.

2 Claims, 15 Drawing Sheets

Photograph of prototype heart valve

(51) Int. Cl.
*A61L 27/18* (2006.01)
*A61L 27/50* (2006.01)
*A61F 2/82* (2013.01)
*B29L 31/00* (2006.01)

(52) U.S. Cl.
CPC ............... *A61L 27/18* (2013.01); *A61L 27/50* (2013.01); *A61L 27/507* (2013.01); *B29C 39/003* (2013.01); *B29L 2031/7534* (2013.01); *Y10T 29/49405* (2015.01)

(56) References Cited

U.S. PATENT DOCUMENTS

| | | | |
|---|---|---|---|
| 4,886,787 A | | 12/1989 | de Belder et al. |
| 5,080,668 A | * | 1/1992 | Bolz et al. ................... 623/2.28 |
| 5,509,930 A | | 4/1996 | Love |
| 6,117,169 A | * | 9/2000 | Moe .............................. 623/2.12 |
| 6,126,686 A | * | 10/2000 | Badylak .............. A61L 27/3691 |
| | | | 623/1.24 |
| 6,174,331 B1 | * | 1/2001 | Moe ...................... A61F 2/2412 |
| | | | 623/2.12 |
| 6,932,787 B2 | | 8/2005 | Cowan et al. |
| 7,744,914 B2 | | 6/2010 | Li et al. |
| 7,767,222 B2 | | 8/2010 | Calhoun et al. |
| 2002/0082689 A1 | | 6/2002 | Chinn |
| 2003/0069635 A1 | | 4/2003 | Cartledge et al. |
| 2005/0027348 A1 | | 2/2005 | Case et al. |
| 2005/0055079 A1 | | 3/2005 | Duran |
| 2005/0113910 A1 | * | 5/2005 | Paniagua et al. ............ 623/2.14 |
| 2006/0142853 A1 | * | 6/2006 | Wang et al. ................. 623/1.46 |
| 2007/0299510 A1 | * | 12/2007 | Venkatraman ........ A61F 2/0077 |
| | | | 623/1.44 |
| 2009/0105804 A1 | | 4/2009 | Shifrin et al. |
| 2009/0209982 A1 | | 8/2009 | Hoerstrup et al. |
| 2010/0057197 A1 | * | 3/2010 | Weber ..................... A61L 27/30 |
| | | | 623/1.42 |
| 2012/0323315 A1 | * | 12/2012 | Bruchman et al. .......... 623/2.17 |

OTHER PUBLICATIONS

Hufnagel, C.A. et al, "Experiences with new types of aortic valvular prostheses", Ann Sur, 1958, vol. 147(5), pp. 636-644.

Schoen, F.J., "Aortic valve structure-function correlations: role of elastic fibers no longer a stretch of the imagination", J Heart Valve Dis, 1997, vol. 6(1), pp. 1-6.

Kidane, A.G. et al., "Current developments and future prospects for heart valve replacement therapy", J Biomed Mater Res B Appl Biomater., 2009, vol. 88(1), pp. 290-303.

Yoganathan, A.P. et al., "Fluid mechanics of heart valves", Annu Rev Biomed Eng, 2004, vol. 6, pp. 331-362.

Mackay, T.G. et al., "New polyurethane heart valve prosthesis: design, manufacture and evaluation", Biomaterials, 1996, vol. 17(19), pp. 1857-1863.

Hutmacher, D.W., "Scaffold design and fabrication technologies for engineering tissues-state of the art and future prespectives", J Biomater Sci Polym Ed, 2001, vol. 12(1), pp. 107-124.

Search Report and Written Opinion, PCT/US2012/028764, dated Nov. 29, 2012, 12 pages.

Kidane, A.G. et al., "A novel nanocomposite polymer for development of synthetic heart valve leaflets" Acta Biomaterialia 2009, vol. 5 pp. 2409-2417.

\* cited by examiner

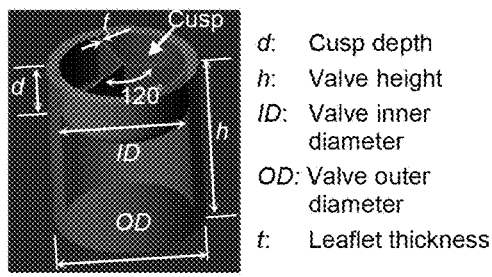

d: Cusp depth
h: Valve height
ID: Valve inner diameter
OD: Valve outer diameter
t: Leaflet thickness Fig. 1 Schematic of proposed heart valve

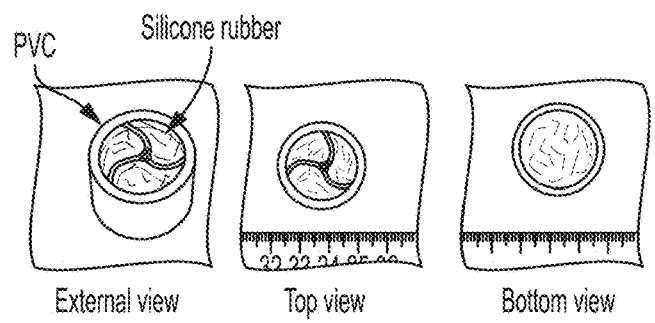

External view · Top view · Bottom view

Fig. 2 Photograph of prototype heart valve

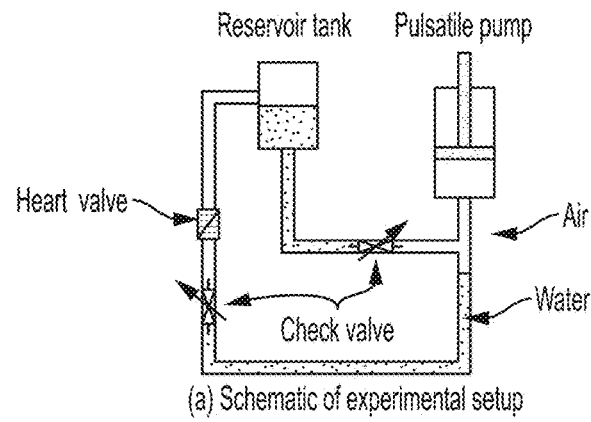

(a) Schematic of experimental setup

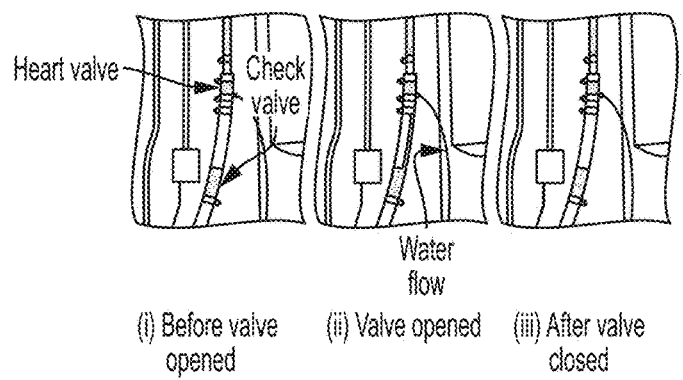

(i) Before valve opened · (ii) Valve opened · (iii) After valve closed (b) Photographs of valve performance Fig. 3 Schematic of experimental setup and photographs of valve testing results

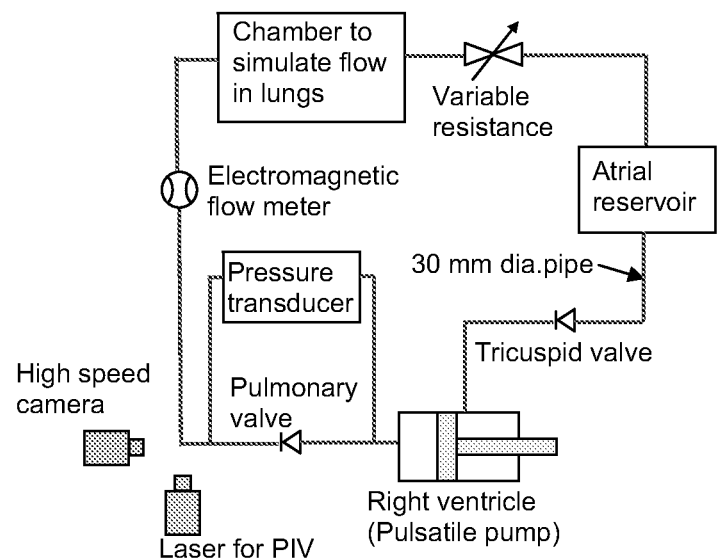
Fig. 4 Schematic of Experimental setup (a) Pressure readout prior to the valve  (b) Pressure readout after the valve

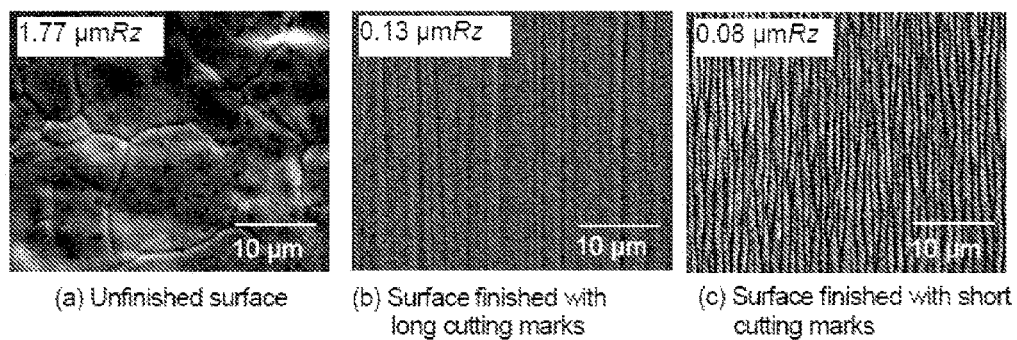
(a) Unfinished surface    (b) Surface finished with long cutting marks    (c) Surface finished with short cutting marks
FIG. 14
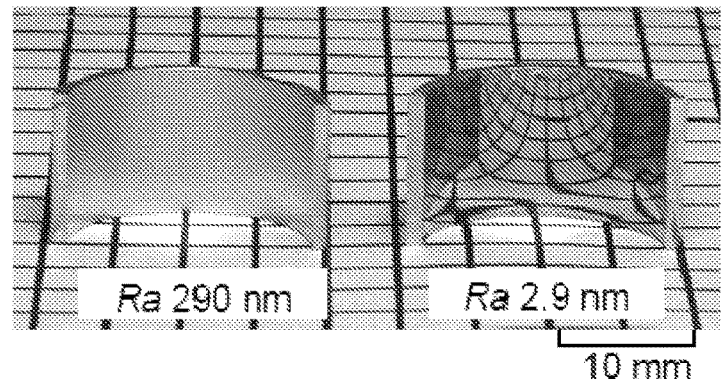
(a) Unfinished surface    (b) Finished surface
FIG. 15   C1220 phosphorus deoxidized copper tube (⌀19.05 × ⌀17.05 ×100 mm)

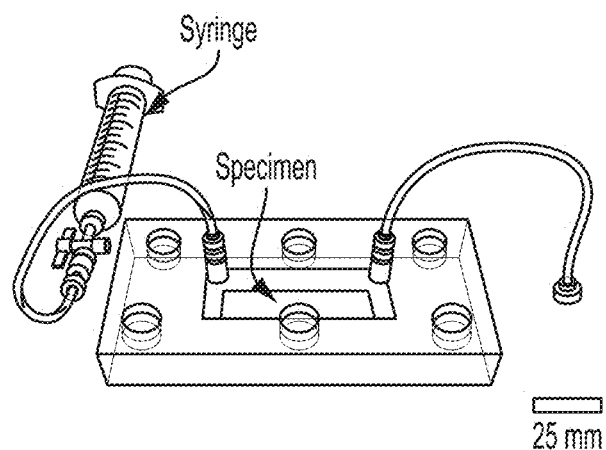
(a) Photograph of flow chamber
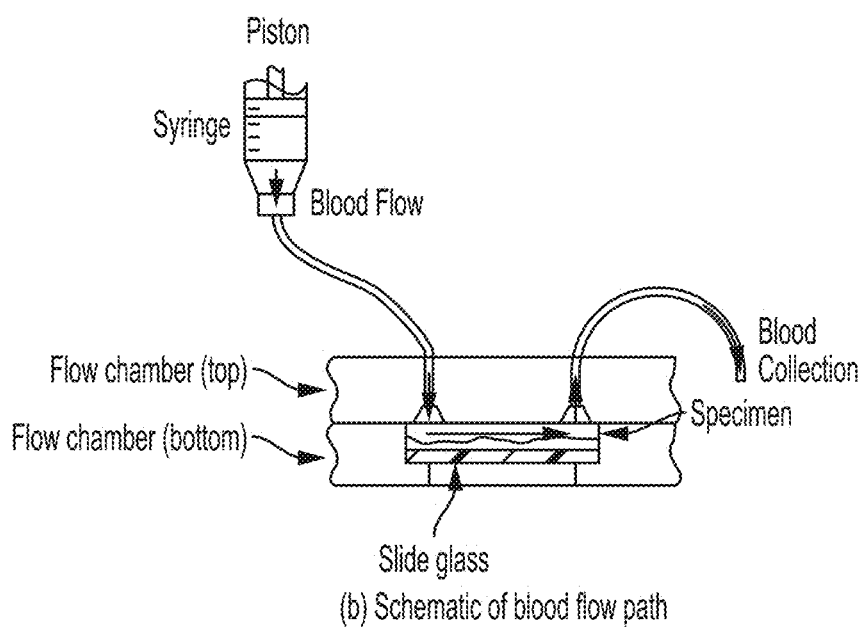
(b) Schematic of blood flow path
FIG. 18

(a) Surface finished with magnetic abrasive with alumina abrasive (5 μm mean diameter)
    Roughness: 1.09 μm Rz, 0.08 μm Ra (b) Surface finished with diamond abrasive (0-0.5 μm)
    Roughness: 0.30 μm Rz, 0.04 μm Ra (a) Surface finished with alumina abrasive (Specimen surface roughness: 1.09 μm Rz, 0.08 μm Ra)

(b) Surface finished with diamond abrasive (Specimen surface roughness: 0.30 μm Rz, 0.04 μm Ra)

ANTI THROMBOGENIC HEART VALVE AND MEDICAL IMPLEMENTS

BACKGROUND

For decades, scientists have attempted to find the perfect artificial heart valve, since the valve could impact the health of thousands of people in the United States alone. Continuous improvement of prosthetic heart valves has been performed since 1953 when Hufnagel performed successful implantation of a prosthetic human valve [1]. In the 1990s it is estimated that 20000 people die each year as a result of valvar dysfunction, and 60000 valve replacement operations are performed annually in the United States [2]. The number of procedures is expected to grow as the outcome of operations for patients with congenital heart disease continues to improve with growth of these individuals into adulthood. Currently available options include biologic valves and mechanical valves, both of which have significant drawbacks: mainly durability and anticoagulation-related issues, respectively. Native heart valves are biologically active tissues that survive well throughout an individual's life, opening and closing over 3 billion times in the average human lifetime. The optimum heart valve replacement should be competent, have a low opening pressure, be durable, not require anticoagulation therapy, have potential for growth, and not induce host reactions to the valve material. Attempts to manufacture the "ultimate" valve have failed to date.

Current options for valve replacement include mechanical valves, tissue engineered valves, animal and human graft valves. Patients with mechanical valves must have daily blood anticoagulation treatments. For tissue heart valves, availability for human use is a paramount concern as well as limited longevity due to host reaction to the valve material with calcification, disintegration and failure of the valve mechanism leading to stenosis and/or incompetence.

The use of polymeric heart valve prostheses dates back to the 1950s, and numerous biomaterials (including silicone, polytetrafluoroethylene (PTEF), and polyurethane (PU) have been tested as leaflet materials [3]. Unfortunately, after many years of experience, problems associated with polymeric heart valve prostheses have not been completely eliminated, demonstrating that none of the developed valves are ideal for replacement procedures [4]. It has been reported that silicone rubbers have been abandoned due to their poor flexural fatigue life, which result from work hardening of the material caused by the cyclic opening and closing of the valve [5, 6]. The tested PTFE and PU valves exhibited abrasive wear associated with calcification and eventually failed [3, 7].

BRIEF DESCRIPTION OF DRAWINGS

FIG. 1 shows a schematic of a heart valve embodiment.

FIG. 2 shows a perspective view, top view, and bottom view of a heart valve embodiment.

FIG. 3 shows a schematic (a) of a system embodiment for testing performance of heart valve embodiments; and photos of certain aspects of the valve operation of the system embodiment.

FIG. 4 shows a schematic of another system embodiment for testing performance of heart valve embodiments.

FIG. 14 shows photos of surface textures of molds using magnetic abrasive finishing.

FIG. 15 shows photos of the inside surface of molds prior to (a) and after finishing according to a finishing method embodiment.

FIG. 18 shows a photo (a) of a system embodiment for testing adhesion to a textured polymeric surface and a schematic (b) of a system embodiment for testing adhesion to a textured polymeric surface.

DETAILED DESCRIPTION

Figure 5:
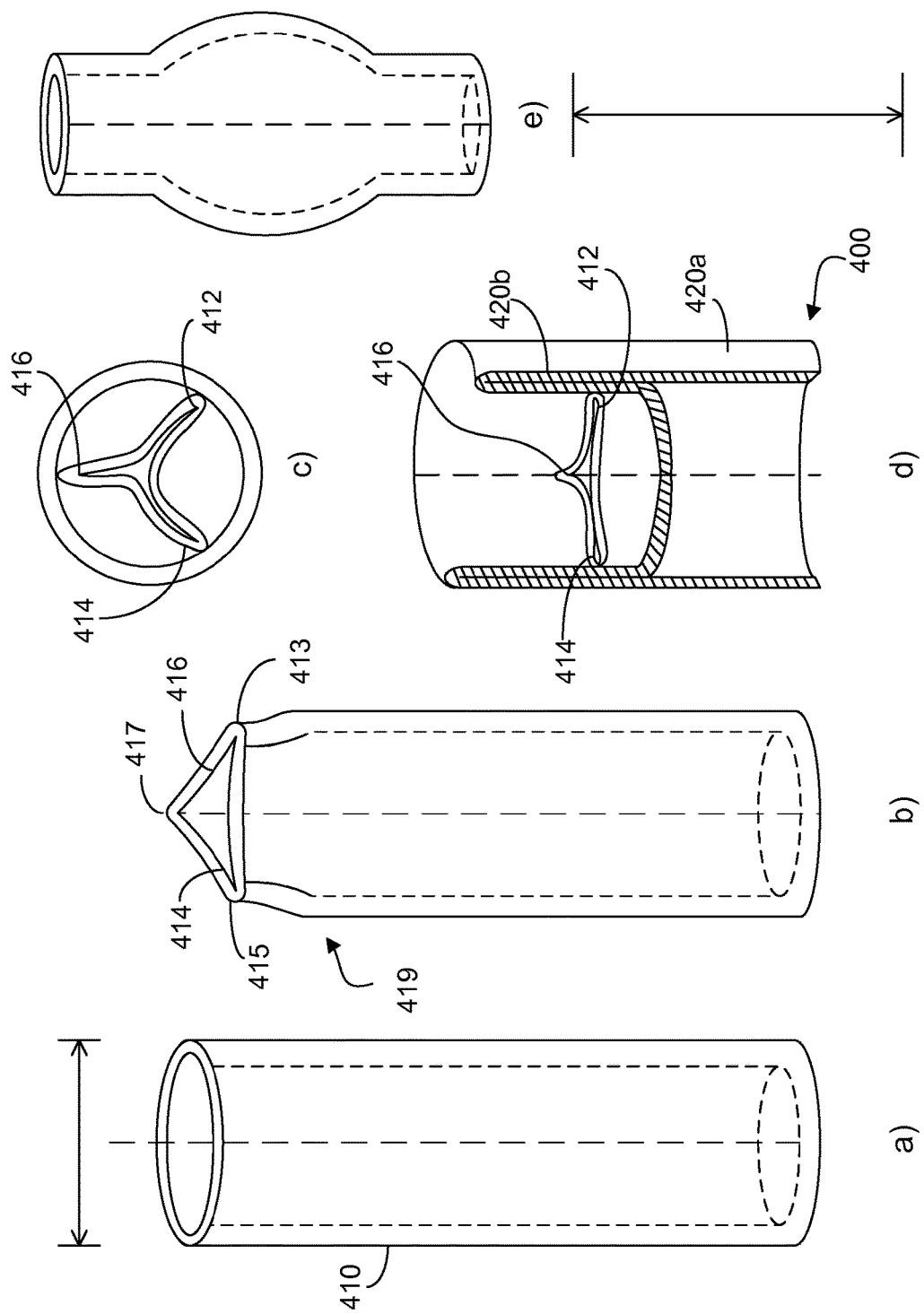
FIG. 5. shows a schematic of a configuration of a unibody heart valve embodiment, including perspective view of blank (a), perspective view of end bending (b), top view of configured valve (c) and cross-section view of configured valve (d), and side perspective view of valve (e).

Despite the fact that silicone rubber replacement heart valves have notoriously failed due to inadequate mechanical properties, the inventors have persisted in trying to develop a viable synthetic heart valve. The invention is based on the significant work by the inventors toward this goal. Accordingly, certain embodiments of the invention are directed to a replacement heart valve that is made from synthetic material(s). In typical embodiments, the synthetic material includes polymeric materials such as silicone or other related polymers or rubbers. The synthetic heart valves of the present invention include a unique surface profile that surprisingly increases the operability of the synthetic heart valve that overcomes many of the deficiencies exhibited by past polymeric heart valves. In a particular embodiment, the heart valve includes a surface profile that comprises a peak to valley roughness of 2 microns or less. This unique surface profile significantly reduces the trapping of blood components, such as platelets, and reduces coagulation potential of the blood on the valve.

Furthermore, according to certain embodiments, the heart valve may be made of a unitary construction that lacks the need for stitching, glue or similar types of fastening. The unique unitary construction also physically simulates the operation of natural heart valves, that is, they include a number of leaflets, typically three, that open and close much in the same way natural valves operate. To the inventors' knowledge, the present application is the first disclosure of a fully synthetic unitary valve design that operates in this manner.

According to one embodiment, a replacement heart valve is provided that includes an outer casing defining an inner channel; and two or more leaflets disposed within the channel and associated with the outer casing. Typically, at least a portion of the two or more leaflets and inner channel include a surface profile having a peak to valley roughness of 2000 nanometers or less, and/or an average roughness of 1000 nanometers or less. In a more specific embodiment, the two or more leaflets include three leaflets. Moreover, the inner channel may be cylindrical and the three leaflets may be arranged around the channel 120 degrees apart. The two or more leaflets are usually configured so as to encourage flow in one direction through the inner channel.

In a more specific embodiment, the two or more leaflets of the embodiment described in the preceding paragraph are comprised of a polymer material. The polymeric material may include, but is not limited to silicone polytetrafluoroethylene (PTFE), polyurethane (PU), polyvinyl alcohol (PVA), etc. The two or more leaflets are typically constructed from a single piece of material. The two or more leaflets may be comprised of, but not limited to, a polymeric material such as silicone. In an even more specific embodiment, the single piece of material is a cylindrical silicone tube having a perimeter that is bent at two or more locations along the perimeter.

According to another embodiment, a heart valve is provided include a surface profile comprises a peak to valley roughness of 1500, 1400, 1300, 1200, 1100, 1000, 900, 800, 700, 600, 500, 400, 300, 200, 100, 75, or 50 nanometers of less, and/or an average roughness of 1000, 800, 600, 400, 300, or 200 nanometers or less.

In yet another embodiment, a heart valve is provided that includes an outer casing defining an inner channel; and three leaflets disposed within the channel and associated with the outer casing. Typically, at least a portion of the two or more leaflets and inner channel have a surface profile having a peak to valley roughness of 2000 nanometers or less, and/or an average roughness of 1000 nanometers or less. The three leaflets may be constructed from a single cylindrical tube having a perimeter and is comprised of silicone, the single cylindrical tube being bent at three predetermined locations along the perimeter. Moreover, the single cylindrical tube may be integral to the outer casing. Further still, the outer casing and three leaflets are associated together and interact without a need for an adhesive or fastener.

In yet another embodiment, a method of making a synthetic heart valve is provided. The method includes obtaining a first mold having an inner surface, the inner surface comprising a surface profile having a peak to valley roughness of 2000 nanometers or less, and/or an average roughness of 1000 nanometers or less. A polymeric material is disposed on the inner surface and then cured to form a valve blank having an outer portion defining an inner channel, whereby the outer portion acquires the surface profile of the first mold inner surface to produce a valve treated surface. The outer portion may be bent at two or more locations to produce two or more leaflets. In a more specific version, the method further includes reversing the outer portion such that at least a portion of the valve treated surface lines the inner channel.

In an alternative embodiment, the method embodiment discussed above includes obtaining a second mold having an outer surface with a surface profile of 2000 nanometers or less peak to valley roughness, and/or 1000 nanometers or less average roughness; and positioning the second mold within the first mold. The second mold is typically dimensioned to produce a space between the second mold and first mold; and a polymeric material is disposed in said space.

In a further embodiment, a replacement heart valve is provided that includes an outer casing defining an inner channel; and two or more leaflets disposed within the channel and associated with the outer casing. Typically, at least a portion of the two or more leaflets and inner channel comprise a surface profile having a peak to valley roughness of 2000 nanometers or less, and/or an average roughness of 1000 nanometers or less, and the outer casing and the two or more leaflets are fabricated from a single valve blank of polymeric material. The two or more leaflets may be three or more leaflets. In a more specific embodiment, the inner channel is cylindrical and the three leaflets are arranged around the channel 120 degrees apart. The polymeric material that may be used includes, but is not limited to silicone. In a more specific version, the single valve blank is a silicone tube having a first and second end and a tube channel, wherein the first end is bent at three locations to form three leaflets. In an even more specific version, the valve blank is folded into itself such that the three leaflets are positioned within the tube channel.

According to certain heart valve replacement embodiments, such embodiment include a surface profile that pertains to a peak to valley roughness of 1500, 1400, 1300, 1200, 1100, 1000, 900, 800, 700, 600, 500, 400, 300, 200, 100, 75, or 50 nanometers of less, and/or an average roughness of 1000, 800, 600, 400, 300, or 200 nanometers or less.

According to a more specific embodiment, what is provided is a replacement heart valve including an outer casing defining an inner channel; and three leaflets disposed within the channel and associated with the outer casing, wherein at least a portion of the two or more leaflets and inner channel comprise a surface profile having a peak to valley roughness of 2000 nanometers or less, and/or an average roughness of 1000 nanometers or less. The three leaflets may be constructed from a single cylindrical tube having a perimeter and is comprised of silicone. The single cylindrical tube is bent at three predetermined locations along the perimeter, wherein the single cylindrical tube is integral to the outer casing. In a more specific version, the outer casing and three leaflets are associated together and interact without a need for an adhesive or fastener.

According to another embodiment, a method of making a synthetic heart valve is provided. The method includes obtaining a single tube of a polymeric material, the tube having a first end, a second end, and body portion defining an inner channel. Further, the method involves bending the body portion at two or more locations to produce two or more leaflets; and folding the body portion such that the first end is folded into the inner channel so as to form a valve comprising two or more leaflets positioned within the inner channel with the body portion forming an upstream and downstream conduit respective to the two or more leaflets. According to a more specific version, the tube comprises an outer surface and an inner surface wherein at least a predominance of the outer and inner surfaces comprise a surface profile of 2000 nanometers or less peak to valley roughness, and/or 1000 nanometers or less average roughness.

Figure 22:
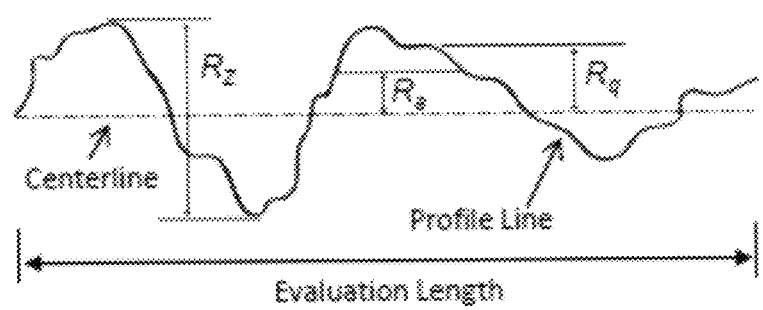
FIG. 22. Shows a diagram that describes different roughness parameters.

By way of background, an example of a surface profile terminology is shown in the diagram of FIG. 22:
The peak-to-valley distance Rz is the largest distance between the highest and lowest points of the profile for a given evaluation length. The average roughness Ra is calculated as the average distance of the profile from the centerline and the root-mean-square (rms) roughness Rq is taken as the root-mean square of the profile distance from the centerline. In light of the teachings herein, one skilled in the art will appreciate that surfaces of heart valve embodiments or medical implements desired to have low thrombogenic activity are designed to possess a peak to valley roughness of 2000, 1500, 1400, 1300, 1200, 1100, 1000, 900, 800, 700, 600, 500, 400, 300, 200, 100, 75, or 50 nanometers of less and/or an average roughness of 1000, 800, 600, 400, 300, or 200 nanometers or less.

EXAMPLES

Example 1. Silicone Heart Valve Embodiment

The tri-leaflet design concept is an attempt to mimic natural human valves. For purposes of this example, the investigators studied the pulmonary valve of a pig. The valve has a diameter of about 15 mm with three 100-200 μm thick cusps. The major difference between pig valves and polymeric valves described in the open literature is the cusp surface conditions. The cusp surface of the pig valve seems to be smoother than that in polymeric valves.
From an engineering point of view, designers of prosthetic heart valves should [4]:
1. minimize the pressure gradient across the valve,
2. minimize the volume of regurgitated blood,
3. avoid regions of high shear stress,
4. avoid regions of flow stagnation upstream or downstream of the valve (Those are prone to thrombus formation.),
5. avoid turbulent flow near the valve (This can be a source of stenosis or regurgitation, depending on the timing of its occurrence during the cardiac cycle.),
6. ensure permanent fusion with the living tissues, and
7. avoid valve failure due to material fatigue, wear, or chemical change.

Accordingly, one valve embodiment is an all-in-one silicone tri-leaflet valve with smooth surfaces that protect the valve from the accumulation of bio-debris. The size of red blood cells, white blood cells, and platelets are about 6-8 μm, 7-25 μm, and 2-3 μm, respectively. To avoid the accumulation of bio-debris, including blood cells, the target surface roughness of the proposed silicone heart valve was set at 0.1-0.5 μm Rz (peak-to-valley). To ease the opening and closing of the leaflets, the heart valve surfaces should have low blood wettability. This condition will also reduce the incidence of thrombosis and extend the effective life of the valve. The surface wettability is also influenced by the surface micro-texture.

Example 2. Manufacture of Prototype Embodiment of a Silicone Heart Valve

According to one embodiment, the fabrication of the valve does not necessarily require plastic injection molding; this avoids complicated mold manufacturing and injection processes. The valve may be made by deforming a single silicone tube, which is made to have various surface textures in the range of nanometers to micrometers. Due to its one-piece construction, this valve does not require any gluing or stitching of components, thereby simplifying the manufacturing process and reducing stress concentrations. The flow of the silicone rubber manufacturing procedure is as follows:

Step 1: Model the desired geometries of the tubes that will be used as surface-texture-copying molds.
Step 2: Machine brass steel tubes and finish the inner and outer surfaces as modeled in Step 1.
The nano/micro-scale surface texture of the inner tube will be controlled by a finishing technique called the Magnetic abrasive finishing process (MAF). This process can control the roughness and texture of the inner and outer surfaces of complex-shaped tubes (e.g., tapered, stepped, and bent) in the range of 10 nm to several μm Rz. MAF will produce the surfaces required for general function of the all-in-one silicone heart valve.
Step 3: Fabricate 100 μm or more thick silicone tubes using the brass steel tube and transfer the tube surface textures to the silicone heart valves.
Step 4: Deform the silicone tubes to fabricate the required heart valve geometry.

TABLE 1

| Specification of tri-leaflet heart v | |
|---|---|
| Material | Bio-compatible silicone rubber |
| Geometry | Tri-leaflet shape (see FIG. 1) |
| | OD: 20-30 mm |
| | ID: 16-26 mm |
| | d: 5-10 mm |
| | t: 0.1-0.2 mm |
| | h: 20-40 mm |
| Opening area | Over ⅔ of cross sectional area of pulmonary artery root |
| Leaflet surface | All-in-one silicone heart valve: 0.1-2.0 μm Rz (peak-to-valley) |
| Pressure | 30-60 mmHg |
| PI | 40% |

The specifications of one specific embodiment are shown in Table 1, and FIG. 1 shows a simplified illustration of the proposed heart valve. In addition to the surface texture requirement, the heart valve must fulfill the requirement of a fluid valve. The effective orifice area (EOA) and the performance index (PI) are calculated according to the following equations [4].

$$EOA = Q_{rms}/51.6\sqrt{\Delta P} \quad (1)$$

$$PI = EOA/A_{SR} \quad (2)$$

where $Q_{rms}$ is the root mean square of the systolic flow rate (mL/s), $\Delta P$ is the mean systolic pressure gradient (mm Hg), and $A_{SR}$ is the valve sewing ring area (cm$^2$). The PI normalizes EOA by valve size and shows how well a valve design utilizes its total opening area. It provides a measure of the valve's resistance characteristics independent of the size.

The valve manufacturing process concept was investigated using silicone rubber (GE Silicone II) and polyvinyl chloride (PVC) tube. This silicone rubber is made for home use (not medical use) and cures in ambient conditions. The PVC support tube is for the trial development testing only. In a more therapeutically more practical embodiment, the valve is made entirely from a single silicone tube, or other physiologically inert material, and will not require the PVC tube for support. The experiments were designed to determine the validity of the proposed procedure to form the all-in-one heart valve and to examine the valve opening and closing characteristics.

FIG. 2 shows photographs of the hand-made prototype valve mounted in a 22 mm ID PVC tube with a wall thickness of 2 mm. The thickness of the leaflets was measured to be between 100 and 200 µm. [The thicknesses, widths and other dimensions can be modified as desired, depending on the patient and medical scenario.] This demonstrates the feasibility of the final two steps of the four-step manufacturing procedure of the heart valves proposed previously. Using this valve, simple fluid dynamic tests were performed to examine the validity of the valve design.

According to another embodiment, the invention pertains to a method of making a synthetic heart valve that includes providing a mold component. The mold component is a hollow conduit that has an interior surface which has undergone a unique surface treatment that achieves a desired roughness profile. The interior surface is coated with a synthetic material that cures onto the interior surface to produce a valve blank having an outer and inner surface. Upon curing, the outer surface of the valve blank adjacent to the mold acquires the surface profile of the interior surface of the mold, whereby the outer surface is then referred to as the treated valve surface. Alternatively, the interior surface of the mold is treated such that there is a gradient roughness profile, i.e. transitions from a region of higher roughness to a region of lower roughness. The valve blank is then typically turned inside out (reversed) such that at least a portion of the treated valve surface is now inside the valve blank. The reversed valve blank is then mechanically bent at two or more strategic locations along its edge to produce leaflets. In a more specific embodiment, the valve blank is folded at three locations located 120 degrees apart to produce three leaflets of a similar shape and size that interact together to encourage flow through the valve blank in a single direction. See Appendices A (FIG. 1) and B.

Example 3. Fluid Dynamic Test of Prototype Valve

FIG. 3 (a) shows a diagram of the pulsating experimental system used for testing flow through the valve. The system incorporates a pneumatic pulsatile pump that generates 50 pulse/min. It consists of an electric motor connected to a piston and cylinder, 90 mm in diameter, which generate the pulses of air. The stroke volume (volume per piston stroke) is adjustable up to 700 mL. FIG. 3 (b) shows the valve performance under the conditions of 50 pulse/min with stroke volume of 200 mL. They show that the water was pushed through the center of valve, and that the valve closed and held the water. The experiments demonstrated the validity of the prototype valve design. The measurement of the flow rate, pressure drop and detailed observation of the flow will be conducted in the proposed research.

Static fluid tests were also performed to examine the valve design feasibility. The first static test was performed with an aqueous solution of 35 vol % glycerol (density 1.085 g/cm$^3$) wherein the solution was left in a tube above a prototype valve for 16 hours at a pressure of 46.6 mmHg (584.2 mm glycerol solution height); the drop in the fluid level was checked at the end of the test. After 16 hrs, the solution had leaked through the center of the cusps by 12.7 mm. Secondly, the burst strength was measured filling the tube above the valve with water until the valve opened. The burst strength was measured to be 233.25 mmHg.

Accordingly, the feasibility of the valve design was demonstrated by in vitro static and dynamic fluid motion tests conducted over short time periods. Although the experiments did not evaluate the valve geometry and surface conditions in detail, these parameters must definitely affect the valve performance. Further study in the proposed research effort will determine the steps necessary to control the precise geometry and surface texture and roughness of the valve. Of paramount importance is to demonstrate effective operation and life span of the heart valve through in vivo tests. These efforts will be continued in the proposed research.

FIG. 4 shows a schematic of another fluid dynamics testing system for the developed heart valve. The piping is fabricated from transparent Plexiglas, and the instruments are connected to a personal computer running LABVIEW. The reciprocating pulsatile pump ensures a frequency of 60-70 pulse/min, corresponding to the frequency of a human heart. The output flow rate is 6 L/min. The pressure at the aortic pipe will vary between 80 and 120 mm Hg (equivalent to the human aortic pressure). An aqueous solution of glycerol (35% by volume) will be the working fluid. This has a density of 1060 kg/m$^3$ and a dynamic viscosity of around $3.2\times10^{-3}$ Pas and is thus a good analog to human blood.

(1): Evaluation of regions of turbulent, cavitating, or stagnant flow in the flow field around the valve: The flow field determination is performed by a particle image velocimeter (PIV in the wish list) and a high-speed camera. The use of the high-speed camera enables one to capture the leaflet motion during opening and closing phases, and the resultant leaflet shape can be plotted. This necessitates the employment of a transparent polycarbonate test chamber and piping throughout the closed system. The PIV is used for making two-dimensional fluid velocity measurements inside and in the immediate vicinity of the silicone tri-leaflet heart valve. The PIV system consists of a low-energy laser beam with an articulated laser arm to direct the laser to the area of investigation. Small-diameter (1-20 µm) fluorescent polymeric or aluminum tracer particles are used for recording the image using a video camera. This technique provides instantaneous velocity vectors of the flow in the valve region. From the instantaneous velocity vectors, the turbulence intensities and Reynolds stresses can be computed and plotted.

(2): Measurement of the pressure gradient: Pressure gradient measurements across the valve are made using a calibrated differential pressure transducer. The pressure values at various locations of the loop can also be recorded using pressure transducers. The following equation is used to predict the pressure gradient [8].

$$\Delta P=(\rho/2)(V_2^2-V_1^2)+(\rho L/A)(dQ/dt) \quad (3)$$

where $V_2$ is the fluid velocity before the valve, $V_1$ is the fluid velocity after the valve, and $\rho$ is the density of the fluid, L is the distance between the pressure taps, A average cross-sectional area between pressure measuring taps, Q is the systolic flow rate at the instant $\Delta P$ occurs, and t is the systolic time.

The EOA and PI will be calculated according to Eqs. (1) and (2).

(3): Endurance and fatigue testing: During testing, the opening and closing of the heart valve is continuously performed over weeks and months, and the pressure and flow velocity is measured continuously. After the test, the surface texture of the heart valve is observed by optical microscopes and a scanning electron microscope. The changes in the thickness of the leaflets will be measured.

These data are fed back to the heart valve manufacturing processes and used for improvement of the heart valve design.

Example 4. Valve Design with Integrated Conduit

Shown in FIG. 5 is alternative embodiment of a heart valve 400 that comprises a unibody construction. The embodiment is crafted from a single piece of polymeric material, such as silicone. In a first step (FIG. 5a), a single tube 410 of polymeric material is produced according to the methods described above. Once the tube 410 is formed, leaflets are formed at one end by clamping (FIG. 5b). In the embodiment shown, three leaflets 412, 414 and 416 are formed by clamping at three different locations 413, 415, and 417 along the periphery of the tube. The three locations 413, 415 and 417 are typically spaced at 120 degrees apart.

Upon clamping of the tube 410 to form leaflets 412, 414, and 416, the tube end 419 is folded inwardly such that the leaflets 412, 414, and 416 are encased within the walls of the tube 410 (FIGS. 5c and 5d, cross section along A-A). As shown, the leaflets 412, 414 and 416 are positioned such that tube walls form a conduit 420 in fluid communication with the leaflets 412, 414, and 416. There is an upstream conduit portion 420a and a downstream conduit portion 420b.

Another advantageous aspect of the valve design 400, apart from the unibody construction, is that the conduit 420 can be adjusted depending on the length of the tube 410. This important advantage allows for the easy manufacture of valves that have varying conduit lengths, which can be customized to form an optimal fit for a specific patient. In addition to tube length, the valve 400 can have varying sizes in the radial axis, which also enables the easy adaptation of valve size for optimal fit in the patient.

The valve design 400 provides for implementation of the polymeric material to serve as the conduit, as opposed to attaching the leaflets within a separate conduit piece. Also, the valve 400 can be produced having variable diameters along its length. This can be controlled by the shape of the tube 410.

Example 5. Heart Valve Fabrication and Testing Embodiment

Valve Fabrication

Figure 6:
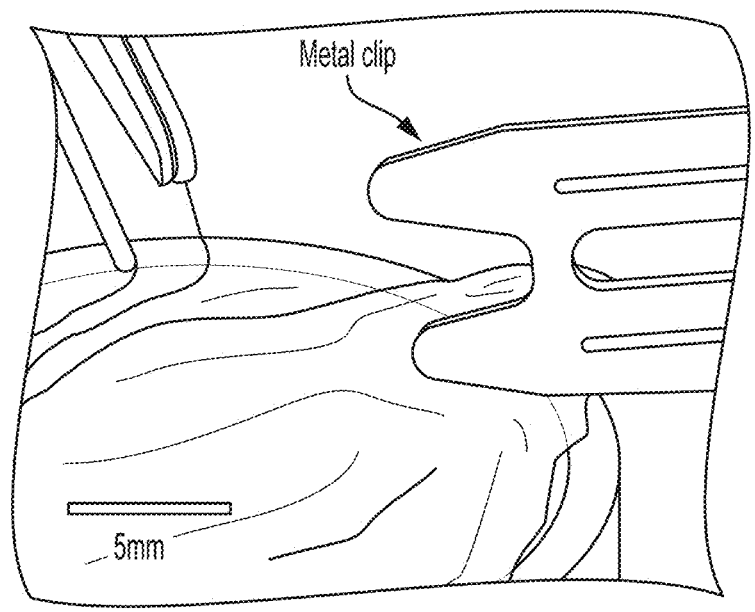
FIG. 6 shows a photo of a valve bending method embodiment.
Figure 7:
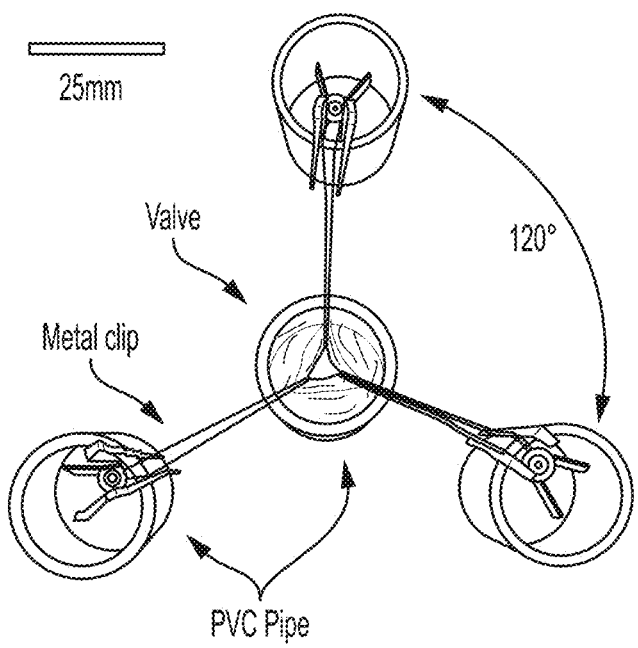
FIG. 7, shows a photo, top view, of valve leaflet configuration.

With the introduction of a new clipping mechanism to the manufacturing process, the uniformity of the leaflets has improved. As shown in FIG. 6, each leaflet is formed by pinching and adhering an approximately 10 mm by 2 mm section of the silicone. This setup provides the valve its needed flexibility while allowing the leaflets to be manipulated and adhered to the silicone's external wall, completing the valve. The new metal clips are currently supported by three pieces of pipe, as shown in FIG. 7. This new setup has the ability to support the weight of the clips while allowing almost complete control of the leaflet position during curing.

Eight valves were tested using a column of water. Two valves were destroyed during the process, and six held water with varying degrees of success. Of the six valves that held water, only one valve prevented a constant stream of water from flowing through the valve. Video clips from the tests and associated comments can be seen in the accompanying video.

Figure 8:
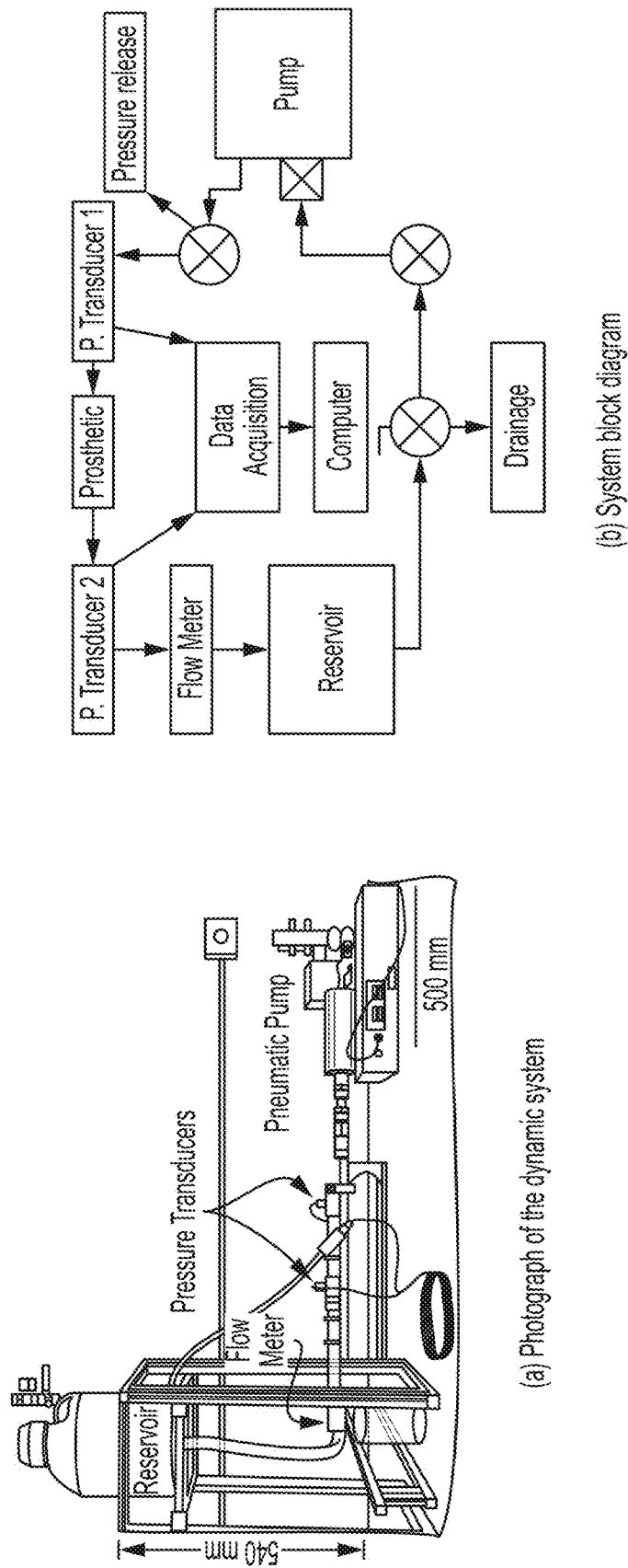
FIG. 8 shows a photo of a system embodiment for testing valve performance.

A pneumatic pump was connected to the dynamic system circuit to perform dynamic tests. The setup is shown in FIG. 8. The pump pushes the fluid through a release valve, the first pressure transducer, the prosthetic valve, and the second pressure transducer. The fluid passes through the flow meter into the reservoir. The pump then draws from the reservoir through a brass check valve and a pneumatic check valve on the pump. The pump, transducers, prosthetic, and flow meter are placed 540 mm below the water level of the reservoir to provide 40 mmHg back pressure to the valve.

Figure 9:
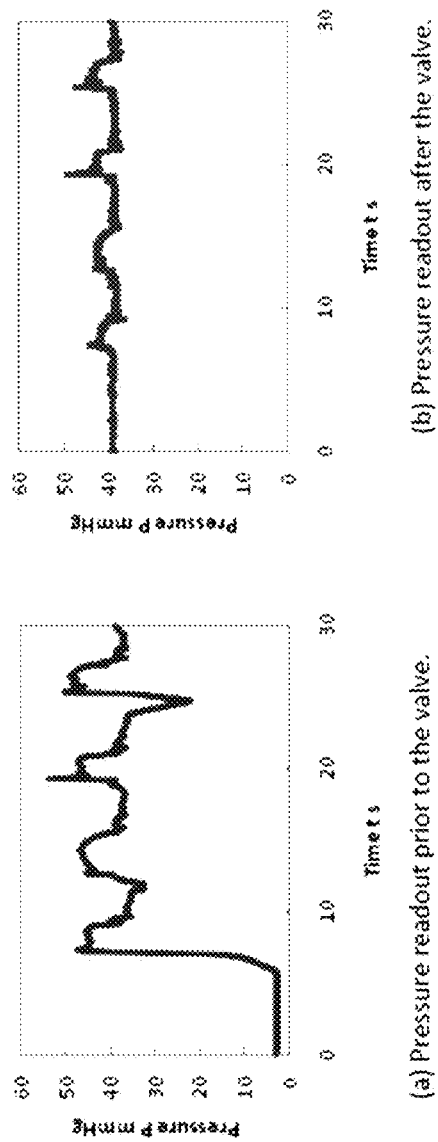
FIG. 9 shows a schematic of a system embodiment for testing valve performance.

During the previous operation, the pressure release valve was manually opened on the backstroke of the pump to create a pressure differential across the valve. The pressure differential across the valve closes the valve leaflets. For the early trials the pump was run at 15 min-1, with a stroke volume of 100 mL. The pressure transducers took 30000 readings at 1000 samples per second. The pump began to run around eight second and the results of the early trials are shown in FIG. 9.

Figure 10:
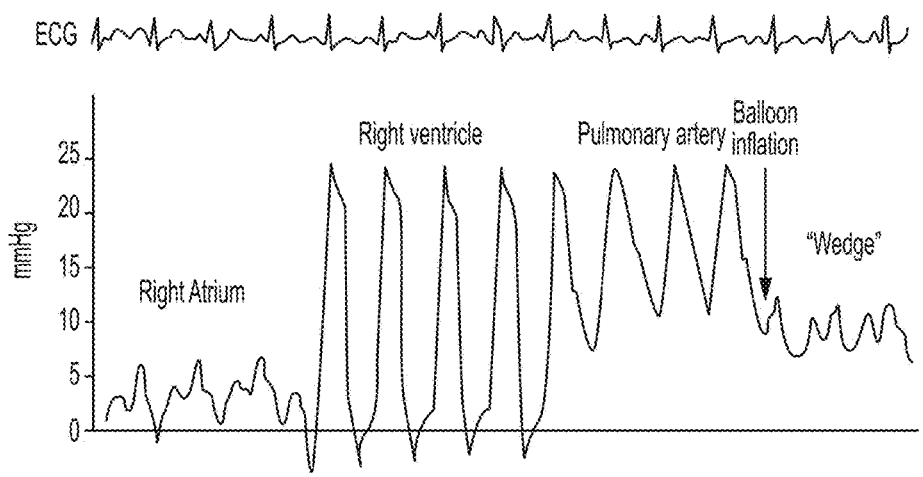
FIG. 10 shows a graph indicating pressures prior to valve (a) and after the valve (b) during a performance test.

FIG. 10 shows the expected pressure profile for the right half of the heart. The pressure profiles before and after the pulmonic valve in FIG. 10 are the right ventricle and pulmonary artery, respectively. From FIGS. 9 (a) and 10, it can be seen that the pressure before the valve does not drop to levels found in the right ventricle, indicating that the pressure might not induce valve closure.

Figure 11:
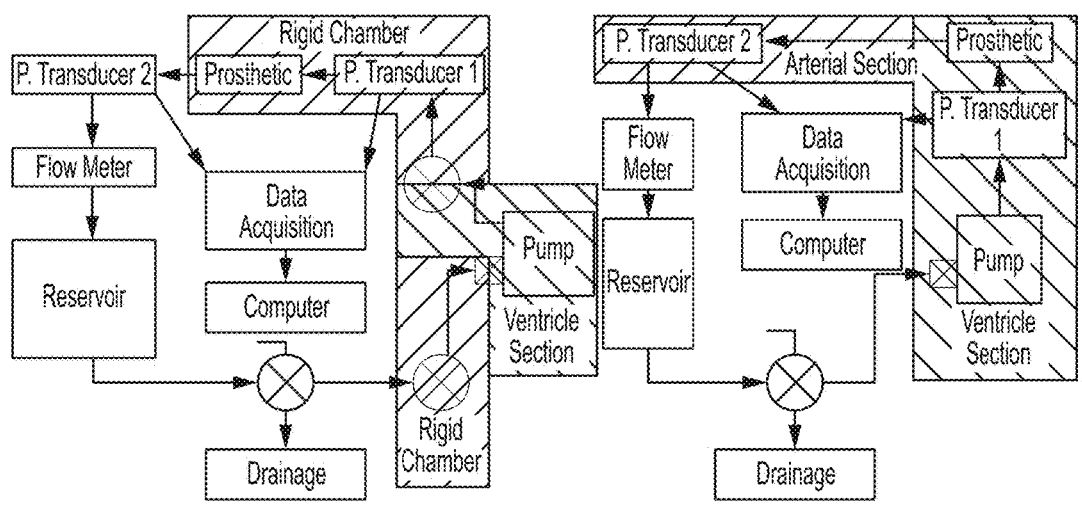
FIG. 11 shows a model pressure profile for an right half of a subject's heart.

FIG. 11 shows circuit diagrams of the system before and after changes were made. The colored blocks represent parts of the circuit meant to mimic physiological components. The pump acts like a ventricle, driving fluid through the system. The initial circuit, as seen in FIG. 11 (a), has two sections, between the release valve and the prosthetic and the two check valves, that act as rigid chambers. These chambers are not present in human anatomy and may affect the pressure profile. The new circuit, shown in FIG. 11 (b), removes the release valve and the check valve not attached to the pump. The ventricular section in the new circuit includes the pump, the first transducer, and the prosthetic. The second transducer in the new circuit reads a pressure analogous to the arterial pressure in FIG. 10.

Figure 12:
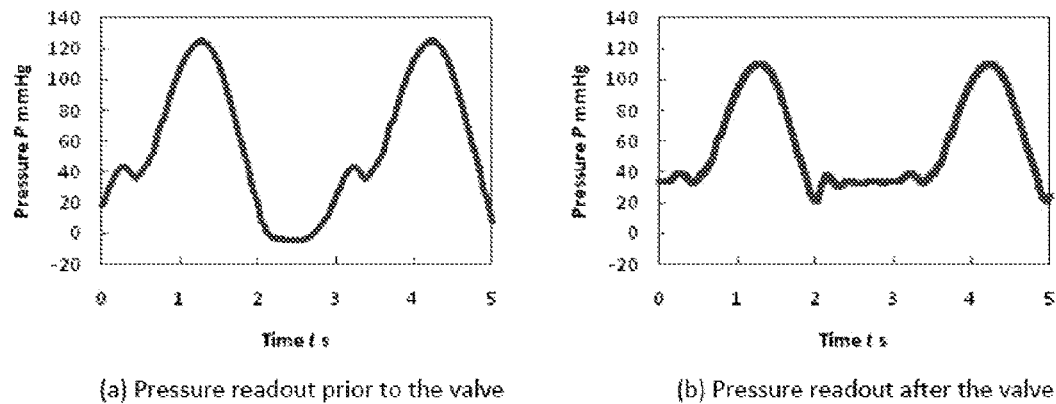
FIG. 12 shows circuit diagrams of another performance testing system embodiment.

FIG. 12 shows the results of trials run on the system shown in FIG. 11 (b). For the trial, the pump was run at 22.5 min-1 at a stroke volume of 100 mL. The pressure transducers took 5000 readings at 1000 samples per second. From FIG. 12 it can be seen that the pressure before the valve drops below zero mm Hg while the pressure after the valve does not drop below 30 to 40 mmHg, indicating the valve closes. The peak pressure is around 120 mm Hg indicating that the prosthetic valve is seeing pressures similar to the aortic valve.

Mold Polishing

A mold brass polishing trial was completed with the new composite abrasive (0-75 µm Fe, 0-0.25 µm diamond) that tracked the changes in brass roughness with finishing time over two polishing phases. The first phase (conditions listed in Table 2) consisted of the new composite coupled with 330 µm iron powder. The brass was finished in 5 min increments until the changes in surface roughness became negligible. The total finishing time for phase 1 was 15 min. The second phase (conditions listed in Table 3), consisted of finishing the brass with only the new composite present. This phase was only completed once, for 5 min.

TABLE 2

Finishing conditions featuring the new composite and 330 µm iron (Phase 1).

| | |
|---|---|
| Workpiece | Brass tube (25.4 × 22 × 90 mm) |
| Workpiece rotation | 2000 min$^{-1}$ |
| Ferrous particles | Electrolytic iron: 2.4 g (330 µm mean diameter) |

TABLE 2-continued

Finishing conditions featuring the new composite and 330 μm iron (Phase 1).

| | |
|---|---|
| Abrasive | New Composite (0-0.75 μm Fe, 0-0.25 μm diamond): 0.6 g |
| Pole | Nd—Fe—B rare-earth permanent magnet (25.4 × 12.7 × 12.7 mm) |
| Pole motion | Amplitude: 5 mm; Frequency: 1.33 Hz (80 min$^{-1}$) |
| Lubricant | 1 mL (initial) 3 mL total |
| Clearance | 1 mm |
| Time | 5 min Increments |

TABLE 3

Finishing conditions featuring the new composite (Phase 2).

| | |
|---|---|
| Workpiece | Brass tube (25.4 × 22 × 90 mm) |
| Workpiece rotation | 2000 min$^{-1}$ |
| Abrasive | New Composite (0-0.75 μm Fe, 0-0.25 μm diamond): 3 g |
| Pole | Nd—Fe—B rare-earth permanent magnet (25.4 × 12.7 × 12.7 mm) |
| Pole motion | Amplitude: 5 mm; Frequency: 1.33 Hz (80 min$^{-1}$) |
| Lubricant | 1 mL (initial) 2 mL total |
| Clearance | 1 mm |
| Time | 5 min Increments |

Results of Mold Polishing

Figure 13:
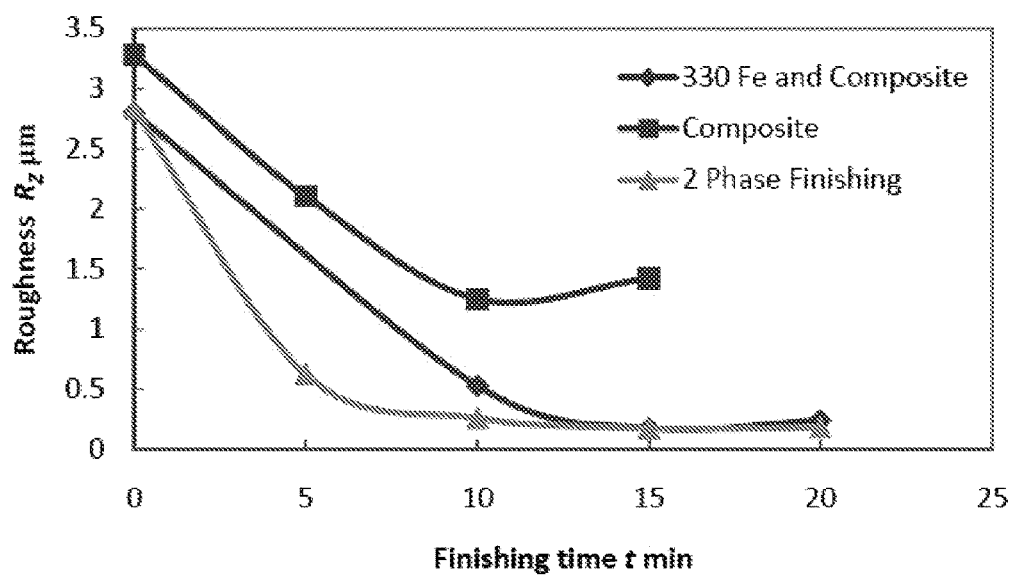
FIG. 13 shows graphs indicating pressures of the valve during performance during testing of a system embodiment shown in FIG. 12.

The change in surface roughness is shown graphically in FIG. 13. The unfinished surface had a peak-to valley roughness of 2.83 μm RZ. The roughness decreased rapidly using the phase 1 finishing conditions before leveling out around 0.2 μm RZ. Also included in the graph are the changes in roughness under the finishing conditions listed in Tables 1 and 2 starting from an unfinished surface. It can be seen that trials using just the new composite initially reduces the roughness but has little effect once the surface reaches a roughness of 1 μm RZ. The trial featuring both the new composite and iron particles behaves almost identically to phase 1 of the 2-phase finishing trial.

Table 4 compares the surface roughness produced under the different finishing conditions previously studied. Finishing the surface with diamond abrasive reduced the roughness the most, to less than 100 nm RZ. Finishing for 15 min with the new composite and iron particles produced a surface roughness of 180 nm RZ.

TABLE 4

Final roughness values of finishing processes.

| Finishing Conditions | Trial | $R_z$ (μm) | $R_a$ (μm) | $R_q$ (μm) | Material removed (mg) | Total finishing time (min) |
|---|---|---|---|---|---|---|
| WA magnetic abrasive | F15W | 0.68 | 0.07 | 0.09 | 65.6 | 10 |
| Diamond paste (0-0.5 μm) | F16W | 0.08 | 0.01 | 0.01 | 117 | 30 |
| Diamond paste (0-0.25 μm) | F17W | 0.09 | 0.01 | 0.02 | 175 | 50 |
| 0-75 μm Composite and Iron | F18W | 0.24 | 0.02 | 0.13 | 117.6 | 20 |
| 0-75 μm Composite | F19W | 1.42 | 0.16 | 0.23 | 35.4 | 15 |
| 2 Phase finishing (Composite and Iron, Composite) | F20W | 0.18 | 0.02 | 0.03 | 89.7 | 20 |

Example 6. Method of Fabricating and Testing Performance of a Valve Prototype

According to another embodiment, a heart valve is fabricated having a surface portion with a desired texture to minimize thrombogenesis. The desired texture is fabricated on the inner and outer surfaces of the mold by means of Magnetic Abrasive Finishing (MAF). In MAF, magnetic abrasive is suspended by magnetic force while conforming to the target surface; this enables the surface finishing of free-form components. The finishing characteristics (including depth of cut of the abrasive, length and directionality of cutting marks, etc.) are controlled by the magnetic field at the finishing area. Local control of the surface texture is also feasible. Moreover, the process enables surface finishing not only the outside but also inside the component (mold). These are distinct advantages of MAF, and the use of MAF to fabricate the mold surface is a significant part of this project. The mold surface textures are precisely replicated on the polymeric component, and the component is folded to form the all-in-one polymeric heart valve. The all-in-one design concept resembles the native valve and does not require that the leaflets be sutured to a supporting ring. This eliminates the interaction of multiple components, and thus minimizes the disturbance of blood flow, and consequently cell lysis and adhesion. The value added to biomedical devices—decreasing the risks of blood-cell adhesion and thrombus formation, for example—is also among the significant innovations of this example.

Wettability of a solid surface by a fluid is determined by the surface energy of the materials and the surface's micro-asperities. In the case of silicone heart valves, the surface texture should be varied according to the desired functions in different regions, such as on the opposite sides of the same leaflet and conduit. For example, to minimize the adhesion of blood cells and to ease the motion of the leaflets, it is important to have low blood-cell wettability, and the lay of the surface texture should be in direction of blood flow. These conditions are attained through the control of micro-scale asperities and directionality of micro-cutting marks of the mold surface. Accordingly, precise control of the wall surface texture of both sides of the double tube structure is one of the key techniques to materialize this concept. Conventional finishing technologies are immature for finishing such intricate sections while controlling the surface texture. A magnetic abrasive finishing MAF has been developed to modify the mold surface texture.

In a magnetic field, magnetic abrasive particles are suspended by magnetic force and link together along the lines of magnetic flux. The magnetic abrasive chains, connected by magnetic force, offer the advantage of a flexible configuration. This enables the magnetic abrasive chain to conform to the workpiece surface, achieving the finishing of stepped, tapered, or free-form surfaces. It is also possible to influence the motion of a magnetic abrasive—even if the particle is not in direct contact with a magnetic pole—by controlling the magnetic field, because the magnetic flux flows unimpeded through the nonferrous workpiece material. This unique behavior of the magnetic abrasive enables the application of the finishing operation not only to easily accessible surfaces but also to areas that are hard to reach by means of conventional mechanical techniques. Controlling the dynamic behavior of magnetic particles varies the surface texture. FIG. 14 shows examples of a variety of surface textures made by MAF inside 304 stainless steel tubes. Even though the finished surfaces exhibit similar surface roughness values, FIG. 14(b) illustrates a surface consisting of long cutting marks, and the surface in FIG. 14(c) consists of shortcutting marks. Many types of materials (such as metals, ceramics, single-crystal materials, and polymers) have been treated using MAF. The control of the processing conditions has taken MAF process into the group of ultra-precision finishing processes. FIG. 15 shows an example of internal finishing of C1220 phosphorus deoxidized copper tube (⌀19.05×§ 17.05×100 mm) [21].

Figure 16:
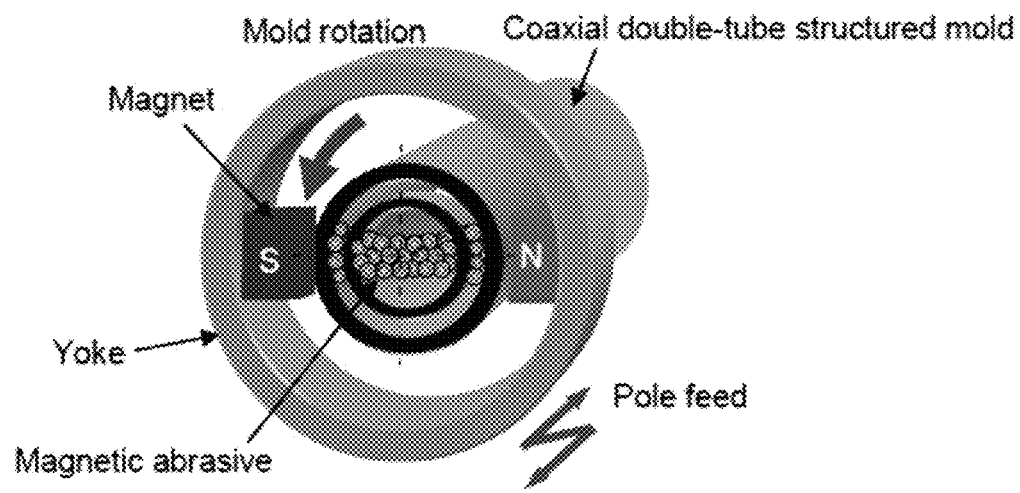
FIG. 16 shows a schematic for a mold finishing method embodiment.

FIG. 16 shows a schematic of the finishing process for the mold designed for this project. The mold will be made of brass, which is nonmagnetic and easily machined. Permanent magnets generate the magnetic field needed for attracting the magnetic abrasive to the finishing area, pressing it against the mold surface. If the tangential component of the magnetic force acting on the magnetic abrasive is larger than the friction force between the magnetic abrasive and the mold surface, the magnetic abrasive shows smooth relative motion against the mold surface when the mold is rotated at high speed. Material is removed from the surface by the magnetic abrasive as a result of this relative motion, and the surface is finished.

The magnetic force F acts on the magnetic abrasive and is shown in the following equation:

$$F = V\chi(H \cdot \mathrm{grad} H) \quad (3)$$

where V is the volume of the magnetic abrasive, $\chi$ is the susceptibility, and H and grad H are the intensity and gradient of the magnetic field, respectively.

The magnetic abrasive is made up of composite particles, which consist of iron and aluminum oxide abrasive. However, this can be replaced by a simple mixture of magnetic particles and conventional abrasive, e.g. diamond abrasive or aluminum oxide grains. According to Eq. (3), the larger the magnetic abrasive or magnetic particles, the greater the magnetic force acting on the magnetic abrasive or magnetic particles is to generate deeper scratches. The scratch shapes and sizes are also affected by the abrasive type and size. Moreover, manipulating the poles along the mold axis causes the magnetic abrasive to move in the axial direction following the motion of the poles. The combination of the magnetic abrasive motion in the axial and circumferential directions produces a cross-hatched pattern.

Figure 17:
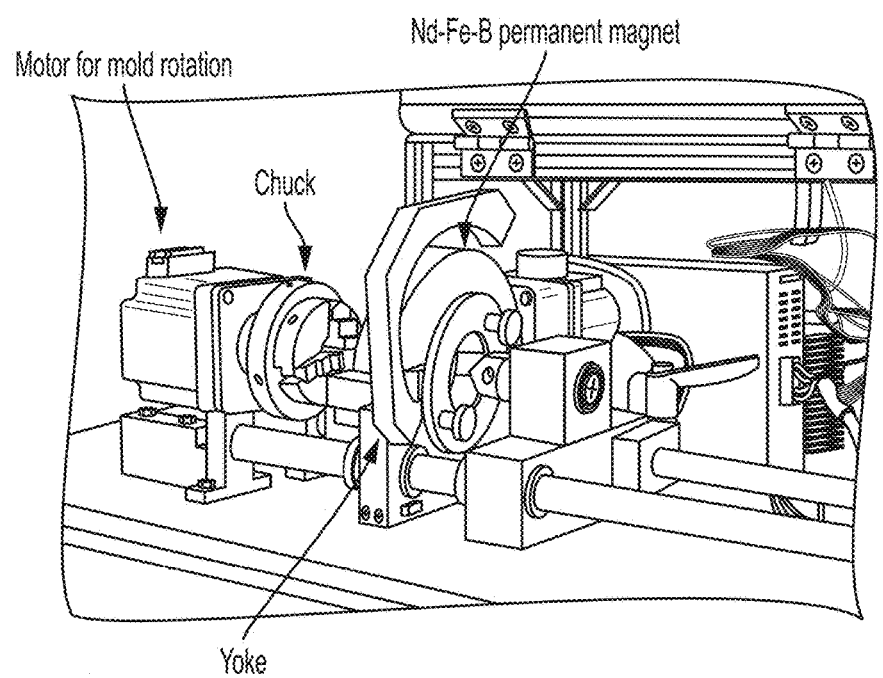
FIG. 17 shows a photo of a system embodiment for conducting a finishing method, such as the method depicted in FIG. 16.

Once the mold surface is conditioned such as by using the machine shown in FIG. 17, silicone is introduced into the mold. After curing for a period of time (e.g. 24 hr), the silicone is removed from the mold. The texture of the mold surface is transferred to the silicone, and the molded component is assembled into a heart valve embodiment, such as that described in other examples.

In vitro blood-cell adhesion tests are performed by techniques such as that taught in Appendix A (see Example 10, infra). The basic concept involves a parallel-plate flow chamber as shown in FIG. FIG. 18. FIG. 18(b) shows the circuit in which the working fluid flows. The blood cell flow over the valve surface is observed using a camera attached to a microscope, shown in FIG. 8. The experimental protocol is as follows:

1. Silicone leaflet (with the surface texture replicated from the mold) is produced one night before the blood-cell adhesion test.

2. The leaflet is cut into a specimen (69×25×0.25 mm), which is placed in the chamber, and the chamber is sealed with vacuum grease.

3. The flow chamber with specimen is set under the microscope.

4. The specimen surface is flushed with phosphate-buffered saline (15 mL) at a flow rate of 100 mL/hr.

5. Fifteen milliliters of whole blood is flushed over the specimen once at a flow rate of 50 m L/h r.

6. The specimen surface is flushed with phosphate-buffered saline (10 mL) at 50 m L/h r.

7. Using cell-imaging system software, the number of red-blood cells and platelets adhered to the specimen surface and the area covered by the adhered cells on the specimen surface are determined. Analysis of the obtained images will suggest the desired surface texture (roughness, micro-asperity shapes, and directionality) that results in the least particle adhesion.

Figure 19:
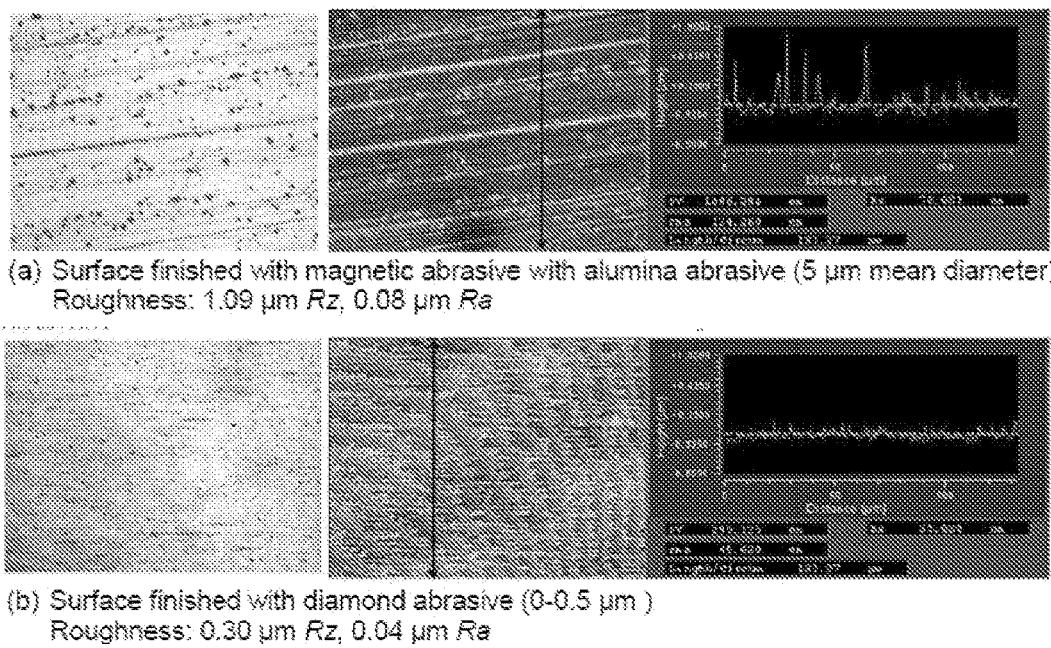
FIG. 19 shows surface profiles of a leaflet specimen prepared using a first mold embodiment (a) and a second mold embodiment (b).

As a separate test, blood-cell adhesion tests may be performed with whole blood to confirm the protocol described above. It has been reported that the shear stress on the aortic valve leaflet surface is in the range of 10-79 dyne/cm2 (1-7.9 Pa) depending on the location [26]. For the first trial in the preliminary blood-cell adhesion test, the blood flow rate was set to obtain shear stress at the lower end, which facilitates blood-cell adhesion on the specimen surface. Under the conditions written in the above protocol, the shear stress was calculated to be 0.83 Pa with the dynamic viscosity of blood of 3.8 cP (0.0038 Pa·s). Two silicone specimens were prepared by replicating the inner surface of tubes (⌀25.4×⌀22×100 mm) and were cut into the specimens (69×25×0.25 mm). FIG. 19 shows the surface textures and profiles measured by an optical profiler.

Figure 20:
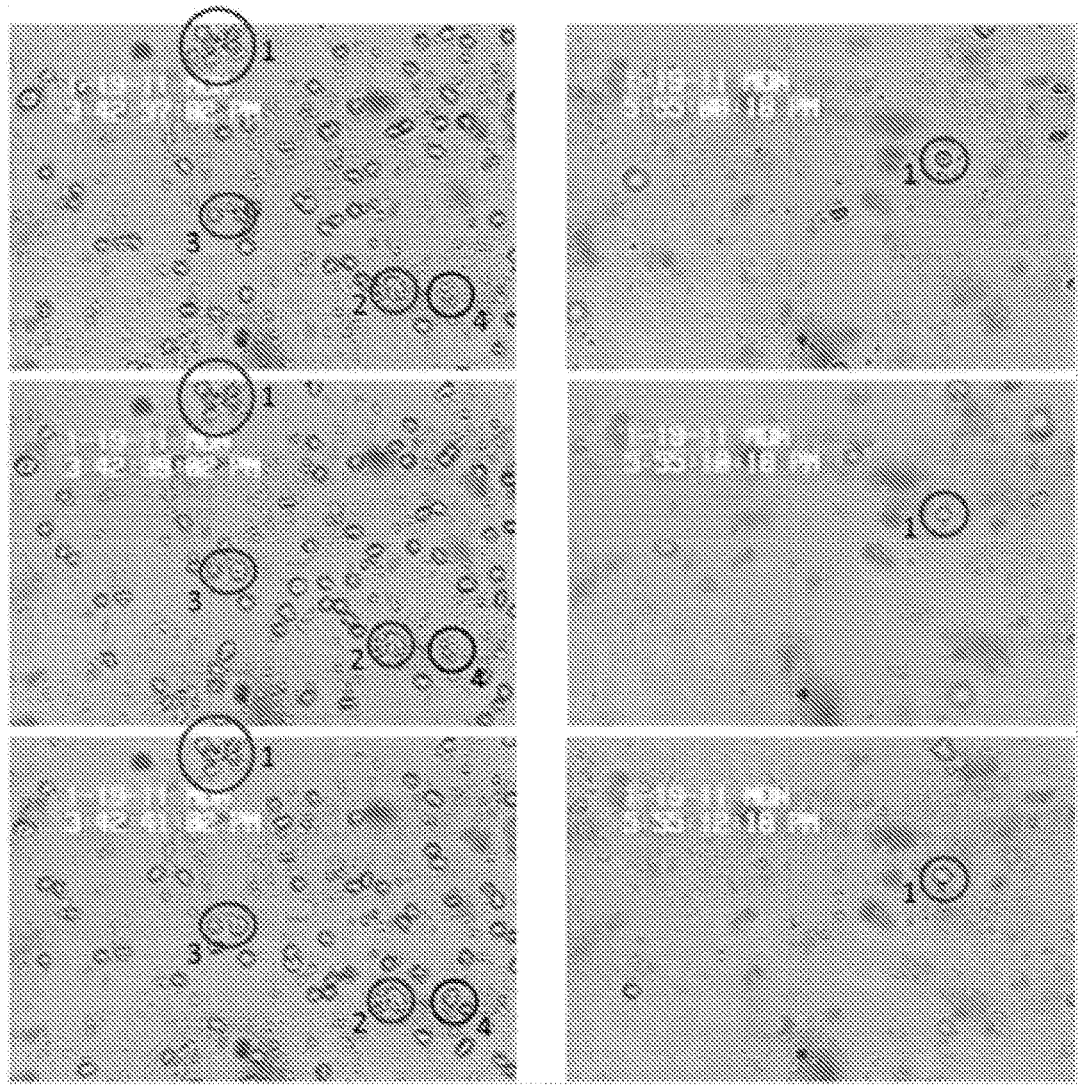
FIG. 20 shows photos of blood cell adhesion on a leaflet specimen (a) and (b) pertaining to specimens (a) and (b), respectively shown in FIG. 19.

FIG. 20 shows photographs of the specimen surface during the blood-cell adhesion tests. A large number of red blood cells and platelets were observed on the specimen with a rough surface finished with alumina abrasive (FIG. 20(a)) while a fine surface finished with diamond abrasive (FIG. 20(b)) clearly discourages blood-cell adhesion. Moreover, these results confirmed the validity of both the experimental setup and protocol.

Example 7. Manufacture of Silicone Valve

Appendix A, pages 1-8, teaches an example of silicone valve manufacturing. In one embodiment, a system for dynamic testing is provided that pertains to a closed loop fluid flow system having a reservoir, flow meter, at least one pressure transducer, and a pump. The prosthetic (e.g. polymeric heart valve) can be placed upstream or downstream the at least one pressure transducer. In a more specific embodiment, a first pressure transducer is positioned upstream the prosthetic and a second pressure transducer is placed downstream the prosthetic. According to one embodiment, a dynamic testing system embodiment is provided as shown in FIGS. 2-5 and 2-6 of Appendix A.

Example 8. Magnetic Abrasive Finishing

Appendix A, pages 9-25, teaches an example of mold finishing using magnetic abrasive finishing. Also, a method of finishing a mold is provided that includes placing a magnetic field around a mold conduit (e.g. cylindrical tube) and disposing magnetic abrasive particles in the conduit. The magnetic abrasive particles are moved along the inner surface of the conduit by rotating the conduit in the magnetic field and/or moving the magnetic field about the conduit. In a more specific embodiment, the magnetic field includes placing a magnet N pole at one location around the conduit and a magnet S pole at a position opposite the one location. In an even more specific embodiment, two magnetic fields are subjected to the conduit. As shown in FIG. 3-1, the magnetic fields produce an intersecting pattern via placements of two N-S pole magnets around the conduit. According to a specific embodiment, a MAF processing system is provided as shown in FIGS. 3-1 to 3-4 of Appendix A. The magnetic abrasive particles range from 100-500 micrometers in size at their largest dimension (typically diameter) and the sample size used ranges from 0.5-5 g. The magnetic abrasive particles used includes but is not limited to, iron particles, WA particles, and diamond particles, or a combination thereof.

Another embodiment provides a method of MAF that includes subjecting a mold surface to the conditions according to that set forth in Tables 3-4, 3-6, 3-7 or 3-8. According to another embodiment, a system and method for determining a surface profile of a finished surface is provided. The method comprises determining the Rz, Ra, and/or Rq of a mold subjected to a magnetic abrasive finishing method.

Example 9. Silicone Leaflet Fabrication

Appendix A, pages 26-32, teaches an example of silicone leaf fabrication. According to one embodiment, a method of leaflet fabrication is provided that includes disposing a polymeric material, such as silicone, to a mold as disclosed in Example 8 and rotating the mold upon deposition of the silicone in the mold. In a more specific embodiment, the mold is rotated at between 200-1000 rotations per minute. In a specific embodiment, the mold is rotated at 600-800 rotations per minute. In an even more specific embodiment, a valve blank is produced according to the conditions set forth in Table 4-1 of Appendix A. One skilled in the art will recognize that the amount of silicone used can be adjusted for larger or smaller mold dimensions based on the ratio provided in Table 4-1 (e.g. (25 outer diameter×22 inner diameter×35 mm length/0.6-0.9 g silicone).

Example 10. Blood Cell Adhesion Testing

Appendix A, pages 33-50 teaches an example of testing blood cell adhesion on silicone leaflets. According to another embodiment, a system and method of testing adhesion to a leaflet surface is provided. A specific example of a system embodiment is shown in FIG. 5-2.

Figure 21:
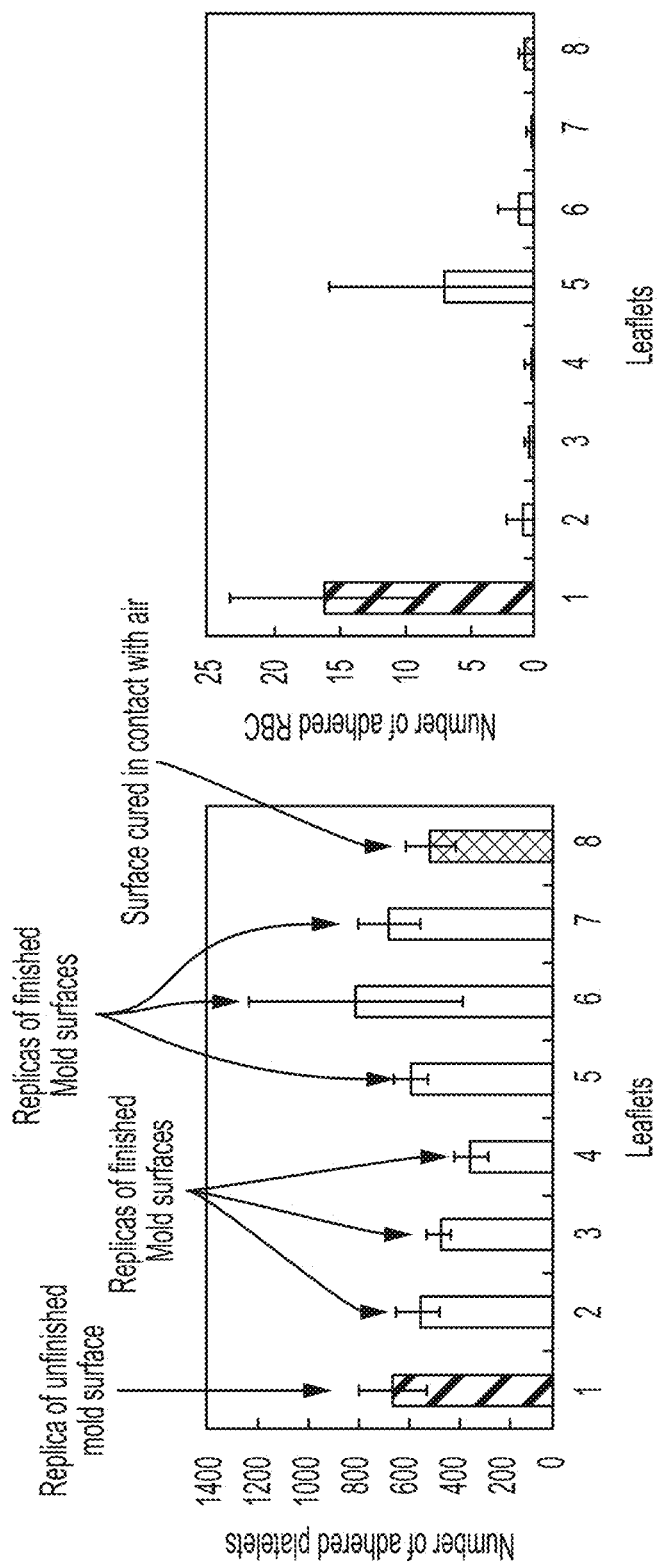
FIG. 21 shows graphs of platelet adhesion (a) and RBC adhesion (b) of different leaflet surfaces.

Furthermore, FIG. 21 shows the results of follow up data showing that silicone surfaces replicated from finished molds had less cell adhesion that silicone surfaces cured in contact with air. This is a surprising discovery since, it would be believed that air cured surfaces would be the most smooth and have the least amount of cell or platelet adhesion.

Example 11. Application of Surface Treatment to Other Medical Applications

In addition to making polymeric heart valves, the fabrication of polymeric materials having a low roughness surface profile can be made for other medical implants and devices. These would include catheters, scopes, implantable luminal structures including shunts, artificial ureters, urethras; barriers designed to prevent adhesions, etc. The medical implement may also comprise instruments or devices that are inserted into the body. The medical implement may comprise at least a surface portion that is anti-thrombogenic. The surface portion may comprise a surface profile roughness of a peak to valley roughness of 2000 nanometers or less and/or an average roughness of 1000 nanometers or less. A mold processed to have a desired surface profile is shaped to create the desired medical implement.

In another aspect, the present invention provides methods for treating and/or preventing surgical adhesions. The surgical adhesions can be the result of, for example, spinal or neurosurgical procedures, of gynecological procedures, of abdominal procedures, of cardiac procedures, of orthopedic procedures, of reconstructive procedures, and cosmetic procedures. The method of preventing the adhesion comprises implementing a medical implement made of a polymeric material having a surface with a peak to valley roughness of 2000 nanometers In one embodiment, the medical implement is made of one or more of the materials from the following non-limited list: silicone, poly-(D,L-lactide-co-glycolide) (PLGA), poly-(dimethylsiloxane) (PDMS), poly-(L-lactide-co-caprolactone-co-glycolide) (FLOG), polycaprolactone (PCL), polylactic acid (PLA), polystyrene, polyurethane, ePTFE, and Dacron.

According to another embodiment, the invention pertains to a medical implantable implement for deployment within a vessel of a mammal patient. The implement has at least one surface coming in contact with blood, said at least one surface comprising at least a portion thereof having a surface profile sufficient to prevent adhesion of thrombogenic proteins thereto. In a more specific embodiment, the surface portion comprises a peak to valley roughness of 2000 nanometers or less and/or an average roughness of 1000 nanometers or less.

In another embodiment, tubes involved in dialysis or in an artificial kidney device comprises a surface portion that is anti-thrombogenic based on a smooth surface profile achieved by the techniques taught herein.

In many instances of practical surgery, it is highly desirable to have a simple means and method for preventing direct contact between tissues and for maintaining this contact-inhibiting effect also during a postoperative period the length of which will vary according to the actual type of surgery involved. Examples of such surgical procedures are manifold, spanning over a wide field: E.g. operations performed in abdominal regions where it is important to prevent adhesions of the intestine or the mesentery with concomitant gastrointestinal disorders; operations performed in the urogenital apparatus where it is important to ward off adverse effects on the ureter and bladder, and on the functioning of the oviduct and uterus; and nerve surgery operations where it is important to minimize the development of granulation tissue. When tendons are operated on there is generally a tendency towards adhesion between the tendon and the surrounding sheath or other surrounding tissue during the immobilization period following the operation. Essentially unsuccessful attempts have been made to solve this problem by using various kinds of sutures and by means of passive movements of the tendon during the healing process. In ophthalmological surgery it is often desirable to have degradable implants at one's disposal which are to be applied in the angle of the anterior chamber of the eye for the purpose of preventing synechiae between the cornea and the iris; this applies especially in cases of reconstructions after severe damaging events. Moreover degradable or permanent implants are often desirable means for preventing adhesion in e.g. glaucoma surgery contexts (preventing adhesion in the subconjunctival filtration space) and in strabismus surgery.

According to other embodiments, a sheet of material having at least a surface portion that is anti-thrombogenic. The sheet can be cut and/or shaped as desired for the target site of need.

The following patents and publications are cited for a few examples of medical implements that can be produced and used in accordance with the teachings herein; information of surgical procedures that benefit from an anti-thrombogenic or anti-adherent medical implement; and materials that can be utilized to make such medical implements:

Cerebrospinal fluid Shunt, U.S. Pat. No. 6,932,787
Vascular implant device, U.S. Pat. No. 7,744,914
Medical implanting devices provided with anti-thrombogenic coating and method for obtaining of such coating, United States Patent Application 20090105804
Non-thrombogenic catheter, U.S. Pat. No. 3,886,947
Method of preventing adhesion between body tissues, means for preventing such adhesion, and process for producing said means, U.S. Pat. No. 4,886,787
Apparatus and method for preventing adhesions between an implant and surrounding tissues, U.S. Pat. No. 7,767,222

The foregoing examples represent a non-limiting list of medical implements that can modified to include at least a portion of their surface that is subjected to the MAF techniques described herein. In essence, a medical implement is an apparatus or instrument that is designed for entry and/or implantation into a body, and/or for transfer of a bodily fluid. The surface treated to acquire a smooth surface profile, such as one to possess a peak to valley roughness of 2000 nanometers or less, or an average roughness of 1000 nanometers or less, would be a surface that comes into contact with a bodily fluid or tissue.

REFERENCES

[1] Hufnagel C A, Villegas P D, Nahas H. Experiences with new types of aortic valvular prostheses. Ann Surg. 1958; 147(5):636-44; discussion 44-5. PMCID: 1450688.
[2] Schoen F J. Aortic valve structure-function correlations: role of elastic fibers no longer a stretch of the imagination. J Heart Valve Dis. 1997; 6(1):1-6.
[3] Kidane A G, Burriesci G, Cornejo P, Dooley A, Sarkar S, Bonhoeffer P, et al. Current developments and future prospects for heart valve replacement therapy. J Biomed Mater Res B Appl Biomater. 2009; 88(1):290-303.
[4] Yoganathan A P, He Z, Casey Jones S. Fluid mechanics of heart valves. Annu Rev Biomed Eng. 2004; 6:331-62.
[5] Chetta G E, Lloyd J R. The design, fabrication and evaluation of a trileaflet prosthetic heart valve. J Biomech Eng. 1980; 102(1):34-41.
[6] Mackay T G, Wheatley D J, Bernacca G M, Fisher A C, Hindle C S. New polyurethane heart valve prosthesis: design, manufacture and evaluation. Biomaterials. 1996; 17(19):1857-63.
[7] Hutmacher D W. Scaffold design and fabrication technologies for engineering tissues—state of the art and future perspectives. J Biomater Sci Polym Ed. 2001; 12(1):107-24.
[8] Yoganathan A P, Corcoran W H, Harrison E C. Pressure drops across prosthetic aortic heart valves under steady and pulsatile flow—in vitro measurements. J Biomech. 1979; 12(2):153-64.

It should be borne in mind that all patents, patent applications, patent publications, technical publications, scientific publications, and other references referenced herein and in the accompanying appendices are hereby incorporated by reference in this application to the extent not inconsistent with the teachings herein.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method of making a synthetic heart valve, the method comprising
obtaining a single tube of a polymeric material formed by casting the polymeric material onto an inner surface of a cylindrical mold, the inner surface of the cylindrical mold having a surface profile comprising a maximum peak to valley distance of 2000 nm or less, the tube having a first end, a second end, and body portion defining an inner channel and comprising an outer surface and an inner surface wherein more than half of each of the outer and inner surfaces comprise a surface profile comprising a maximum peak to valley distance of 2000 nanometers or less as a result of curing onto a mold having the surface profile;
bending the body portion at two or more locations to produce three leaflets;
folding the body portion such that the first end is folded into the inner channel so as to form a valve comprising three leaflets positioned within the inner channel with the body portion forming an upstream and downstream conduit respective to the two or more leaflets.

2. The method of claim 1, wherein the polymeric material is silicone, polytetrafluoroethylene (PTFE), polyurethane (PU), or polyvinyl alcohol (PVA).

* * * * *